US010143835B2

(12) United States Patent
Ejiri et al.

(10) Patent No.: US 10,143,835 B2
(45) Date of Patent: Dec. 4, 2018

(54) BIOLOGICAL ELECTRODE AND BIOLOGICAL ELECTRODE-EQUIPPED WEARING TOOL

(71) Applicant: SMK Corporation, Tokyo (JP)

(72) Inventors: Koichiro Ejiri, Kanagawa (JP); Haruhiko Kondo, Kanagawa (JP)

(73) Assignee: SMK Corporation, Tokyo (JP)

( * ) Notice: Subject to any disclaimer, the term of this patent is extended or adjusted under 35 U.S.C. 154(b) by 0 days.

(21) Appl. No.: 15/627,352

(22) Filed: Jun. 19, 2017

(65) Prior Publication Data
US 2018/0043151 A1 Feb. 15, 2018

(30) Foreign Application Priority Data

Aug. 10, 2016 (JP) ................... 2016-157105

(51) Int. Cl.
A61N 1/04 (2006.01)
A61B 5/00 (2006.01)

(52) U.S. Cl.
CPC .......... *A61N 1/0484* (2013.01); *A61B 5/6802* (2013.01); *A61B 5/6804* (2013.01); *A61N 1/0452* (2013.01); *A61B 2562/0209* (2013.01); *A61B 2562/046* (2013.01)

(58) Field of Classification Search
CPC .... A61N 1/0484; A61B 5/6802; A61B 5/6804
See application file for complete search history.

(56) References Cited

U.S. PATENT DOCUMENTS 4,729,377 A * 3/1988 Granek .............. A61B 5/04085
600/382
2012/0259239 A1* 10/2012 Chenaux ............ A61B 5/04001
600/554

FOREIGN PATENT DOCUMENTS

JP 2005-349021 A 12/2005

* cited by examiner

*Primary Examiner* — William Levicky

(57) ABSTRACT

Provided is a biological electrode and a biological electrode-equipped wearing tool, in which a contact surface having a certain surface area is suitably brought into intimate contact with a living body, and a suitable electrical distribution is obtained. A biological electrode includes: an electrode sheet having a plurality of electrode bodies spaced apart from each other; and a conductive cloth portion superimposed on the electrode sheet. The electrode sheet includes stretching wires that link the neighboring electrode bodies, has a shape of a stretchable and flexible mesh sheet, and can follow a living body to be suitably deformed.

13 Claims, 7 Drawing Sheets

BIOLOGICAL ELECTRODE AND BIOLOGICAL ELECTRODE-EQUIPPED WEARING TOOL

CROSS REFERENCE TO RELATED APPLICATION

The contents of the following Japanese patent application are incorporated herein by reference, Japanese Patent Application No. 2016-157105 filed on Aug. 10, 2016.

FIELD

The present invention relates to a biological electrode and a biological electrode-equipped wearing tool, which are to be contacted with a living body such as the human body mainly for stimulating muscles or measuring physical information.

BACKGROUND

There have been known a therapeutic apparatus in which an electrode is brought into contact with a desired position of the human body to provide electrical stimuli to muscles through the electrode, such as a low-frequency therapeutic device.

A biological electrode used for such a therapeutic apparatus has a problem in that a commonly-used metal electrode is unlikely to ensure sufficient contact surface areas with the human body when brought into contact with the skin, and the contact surface cannot follow the change of the skin shape associated with the movement of the human body.

The contact surface areas with the human body and the properties of following the change of the skin shape have been ensured by placing gauze impregnated with a conductive medium such as a salt solution between the metal electrode body and the skin, and fixing the gauze and the electrode body with a band or the like.

Also, a biological electrode for wearable apparatuses, in which a planar electrode having a certain surface area is formed by weaving a conductive cloth to clothes and is connected to a connection terminal, and the electrode is contacted with a desired position of the human body and follows the skin shape by wearing the cloths has been developed (see JP-A-2005-349021, for example).

SUMMARY

Technical Problem

However, the above-described technologies had a risk that electric currents supplied from the electrode body through the conductive medium such as a salt solution may be dispersed, inhibiting stimuli from being efficiently provided to muscles.

Also, since the planar electrode constituted by a conductive cloth has a certain surface area, there was a risk that a long distance from the actually stimulated position to the connection terminal may cause electric resistance to increase, thereby reducing the output of electrical signals in that portion.

In view of such problems, an object of an embodiment according to the present invention is to provide a biological electrode and a biological electrode-equipped wearing tool, in which a contact surface having a certain surface area is suitably brought into intimate contact with a living body, and a suitable electrical distribution is obtained.

Solution to Problem

For solving the above-described problems, a first aspect of the present invention is a biological electrode which is to be contacted with the surface of a living body and electrically connected to the living body. The biological electrode includes: an electrode sheet having a plurality of electrode bodies spaced apart from each other; and a conductive cloth portion superimposed on the electrode sheet. The electrode sheet includes stretching wires that link the neighboring electrode bodies, and has a shape of a stretchable and flexible mesh sheet.

A second aspect of the present invention is the biological electrode according to the first aspect, in which a portion or all of the stretching wires are conductive stretching wires.

A third aspect of the present invention is the biological electrode according to the first or second aspect, in which the electrode body located in the center of the electrode sheet is connected to equipment.

A fourth aspect of the present invention is the biological electrode according to the first aspect, in which all of the stretching wires are insulating stretching wires, and each of the electrode bodies is connected to equipment.

A fifth aspect of the present invention is a biological electrode-equipped wearing tool, which includes a biological electrode integrated with an insulating cloth portion that constitutes a wearing tool. The biological electrode is brought into intimate contact with the surface of a living body by wearing the wearing tool. The biological electrode includes: an electrode sheet having a plurality of electrode bodies spaced apart from each other; and a conductive cloth portion superimposed on the electrode sheet. The electrode sheet includes stretching wires that link the neighboring electrode bodies, and has a shape of a stretchable and flexible mesh sheet. The insulating cloth portion, the electrode sheet, and the conductive cloth portion are integrated in a layered arrangement.

A sixth aspect of the present invention is the biological electrode-equipped wearing tool according to the fifth aspect, in which a portion or all of the stretching wires are conductive stretching wires.

A seventh aspect of the present invention is the biological electrode-equipped wearing tool according to the fifth or sixth aspect, in which the electrode body located in the center of the electrode sheet is connected to equipment.

An eighth aspect of the present invention is the biological electrode-equipped wearing tool according to the fifth aspect, in which all of the stretching wires are insulating stretching wires, and each of the electrode bodies is connected to equipment.

A ninth aspect of the present invention is the biological electrode-equipped wearing tool according to any one of the fifth to eighth aspects, in which the wearing tool is clothes.

A tenth aspect of the present invention is the biological electrode-equipped wearing tool according to any one of the fifth to eighth aspects, in which the wearing tool is an attachment tool having a shape of a band, a tube, socks, or gloves for covering muscles, joints or ligaments.

The biological electrode according to an embodiment of the present invention includes, as described above, an electrode sheet having a plurality of electrode bodies spaced apart from each other, and a conductive cloth portion superimposed on the electrode sheet. The electrode sheet includes stretching wires that link the neighboring electrode bodies, and has a shape of a stretchable and flexible mesh sheet. Accordingly, the electrode sheet can suitably follow the variation of the surface of a living body in an intimate contact state while ensuring a certain contact surface area with the living body, and multipolarity enables a favorable electrical distribution to be obtained. Thus, dispersion of electrical currents and partial decrease of outputs can be suitably prevented.

Also, since a portion or all of the stretching wires are conductive stretching wires in an embodiment of the present invention, a circuit suitable for an application can be configured depending on a combination of the stretching wires and the insulating stretching wires. Furthermore, when all of the stretching wires are conductive stretching wires, the electrode sheet can have high conductivity.

In addition, since the electrode body located in the center of the electrode sheet is connected to equipment in an embodiment of the present invention, the electric resistance values from the center electrode body to the electrode bodies in the same distance from the center electrode body become uniform, thereby enabling the potential differences among the electrode bodies to be reduced.

Also, since all of the stretching wires are insulating stretching wires, and each of the electrode bodies is connected to equipment in an embodiment of the present invention, the electrode bodies are connected in parallel to equipment, and electric power can be uniformly supplied to the electrode bodies.

Also, in an embodiment of the present invention, the biological electrode-equipped wearing tool includes a biological electrode integrated with an insulating cloth portion which constitutes a wearing tool, and the biological electrode is brought into intimate contact with the surface of a living body by wearing the wearing tool. The biological electrode includes an electrode sheet having a plurality of electrode bodies spaced apart from each other and a conductive cloth portion superimposed on the electrode sheet. The electrode sheet includes stretching wires that link the neighboring electrode bodies, and has a shape of a stretchable and flexible mesh sheet. The insulating cloth portion, the electrode sheet, and the conductive cloth portion are integrated in a layered arrangement. Accordingly, the biological electrode can be brought into intimate contact with a desired position of a living body, and suitably follow the variation of the surface of a living body in an intimate contact state while ensuring a certain contact surface area with the living body. Furthermore, multipolarity enables a favorable electrical distribution to be obtained. Thus, dispersion of electrical currents and partial decrease of outputs can be suitably prevented.

Moreover, in an embodiment of the present invention, a portion or all of the stretching wires are conductive stretching wires, and the electrode body located in the center of the electrode sheet is connected to equipment. Alternatively, all of the stretching wires are insulating stretching wires, and each of the electrode bodies is connected to equipment. Accordingly, a circuit which is optimum for the application of a wearing tool can be designed.

Also, since the wearing tool is clothes in an embodiment of the present invention, the biological electrode can be easily brought into contact with the surface of a living body by wearing the clothes. Furthermore, since the wearing tool is alternatively an attachment tool having a shape of a band, a tube, socks, or gloves for covering muscles, joints or ligaments, the biological electrode can be brought into intimate contact with a local position of a living body according to the purpose.

DESCRIPTION OF EMBODIMENTS

Figure 1:
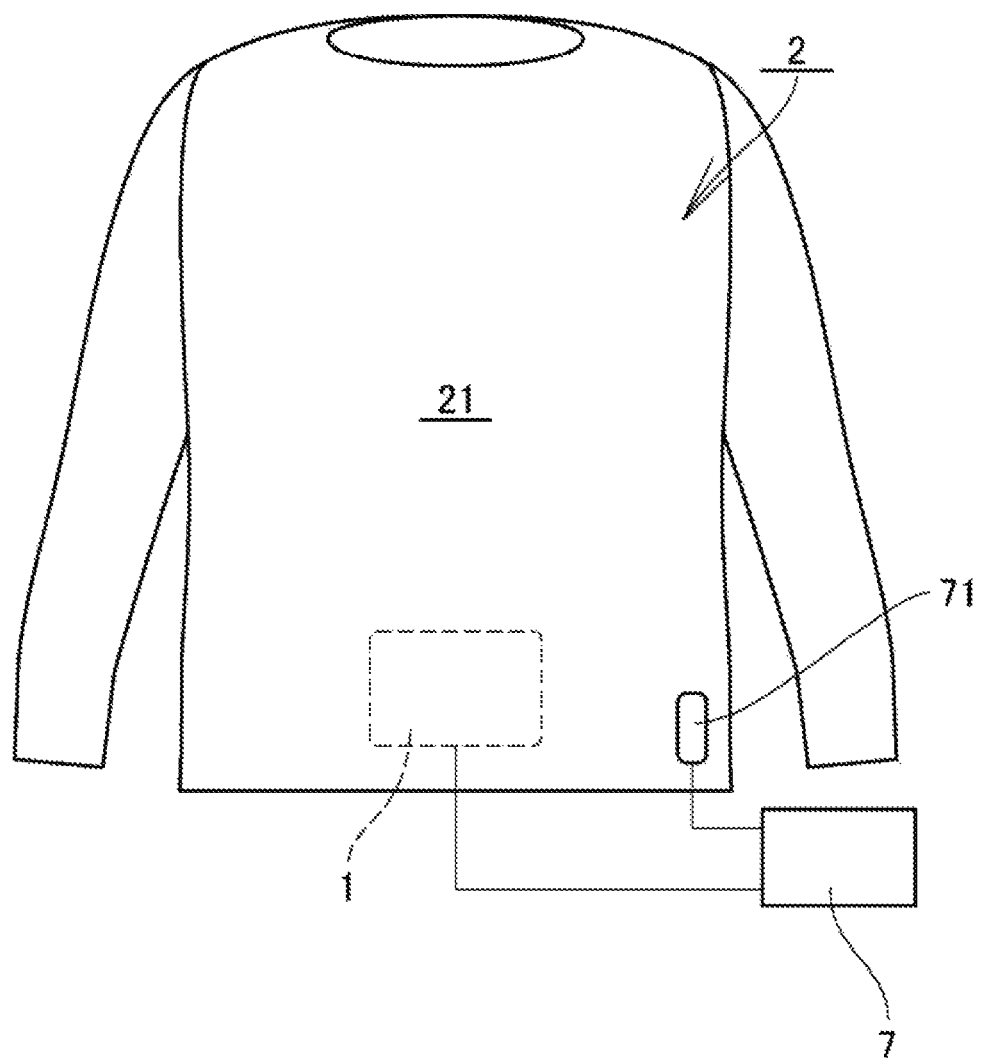
FIG. 1 is a front view illustrating an example of a biological electrode-equipped wearing tool according to an embodiment of the present invention.

Next, embodiments of a biological electrode and a biological electrode-equipped wearing tool according to the present disclosure will be described based on examples illustrated in FIG. 1 to FIG. 4. It is noted that, in the drawings, reference numeral 1 indicates a biological electrode, and reference numeral 2 indicates a biological electrode-equipped wearing tool.

As illustrated in FIG. 1, the biological electrode-equipped wearing tool 2 constitutes an apparatus which includes the biological electrode 1 integrated with an insulating cloth portion 22 that constitutes clothes 21 and which has an electric circuit through a living body by electrically connecting the biological electrode 1 with equipment 7. It is noted that, in FIG. 1, reference numeral 71 indicates a GND electrode to be contacted with a living body 6 or other portions.

The insulating cloth portion 22 has the shape of a stretchable and flexible cloth formed with chemical fibers such as polyester. The clothes 21 have an embodiment which suits an application such as a shirt, a band, and socks formed with the insulating cloth portion 22, and are to be brought into intimate contact with the living body 6 by wearing the clothes 21.

Figure 2:
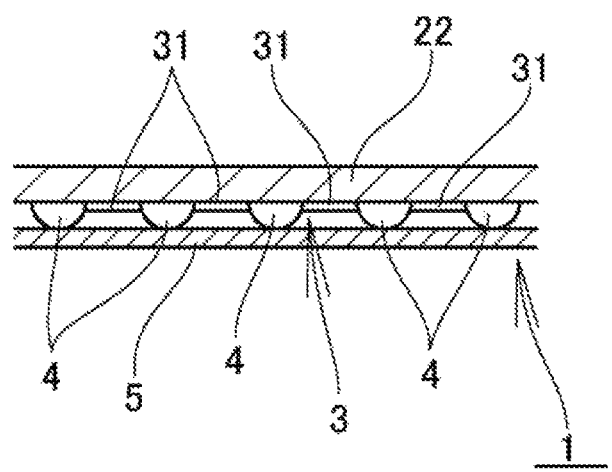
FIG. 2 is a partially enlarged cross-sectional view illustrating a biological electrode in FIG. 1.

The biological electrode 1 includes, as illustrated in FIG. 2, an electrode sheet 3 having a plurality of electrode bodies 4 spaced apart from each other and a conductive cloth portion 5 superimposed on the electrode sheet 3. The conductive cloth portion 5 is to be brought into intimate contact with the surface of the living body 6.

The electrode sheet 3 includes, as illustrated in FIG. 3A to FIG. 6, the hemispherical electrode bodies 4 and stretching wires that link the neighboring electrode bodies 4, and has a shape of a stretchable and flexible mesh sheet.

Each of the electrode bodies 4 is hemispherical and has its surface plated with conductive metal such as gold. The electrode bodies 4 are linked to each other with stretching wires 31 in a conducting state. It is noted that the shape of the electrode bodies 4 is not limited to hemispherical, and may be spherical.

Figure 3A:
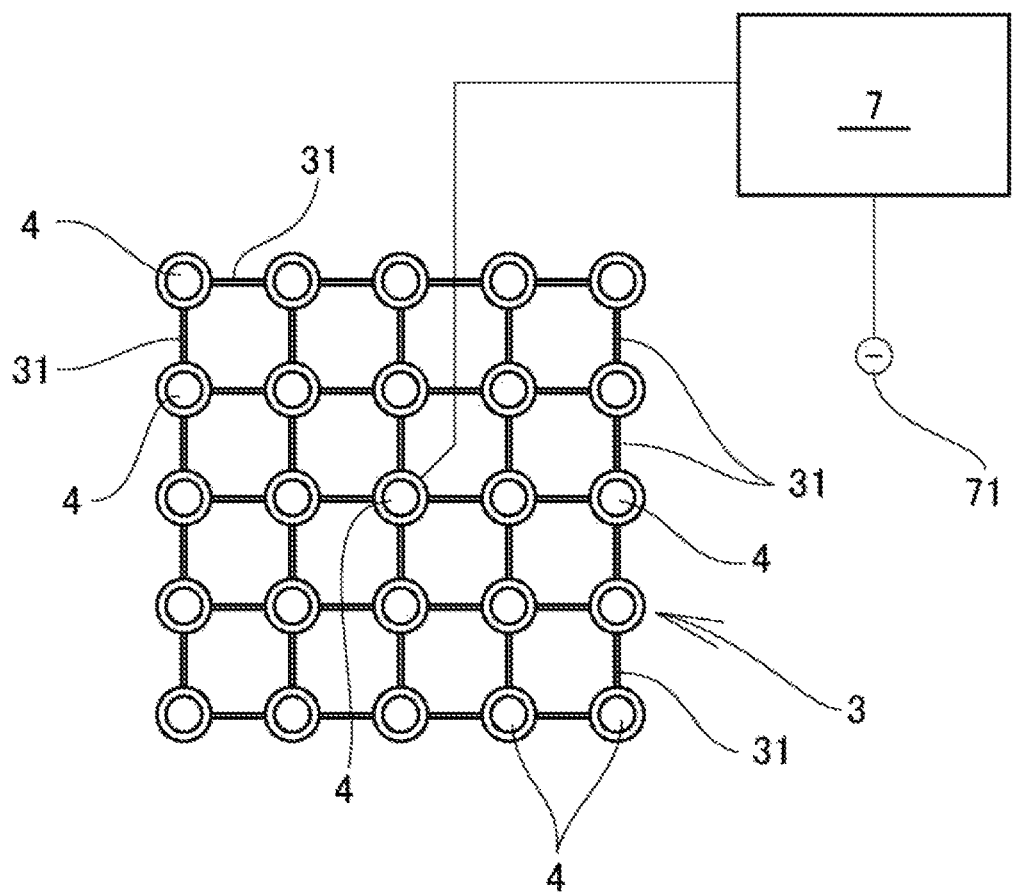
FIG. 3A is a planar view illustrating an example of an electrode sheet.
Figure 3B:
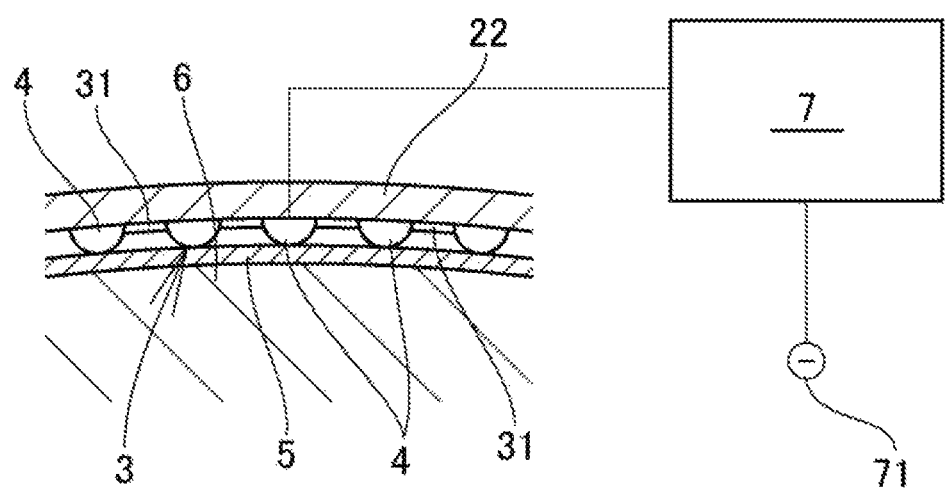
FIG. 3B is a schematic circuit diagram when the electrode sheet is applied.
Figure 4:
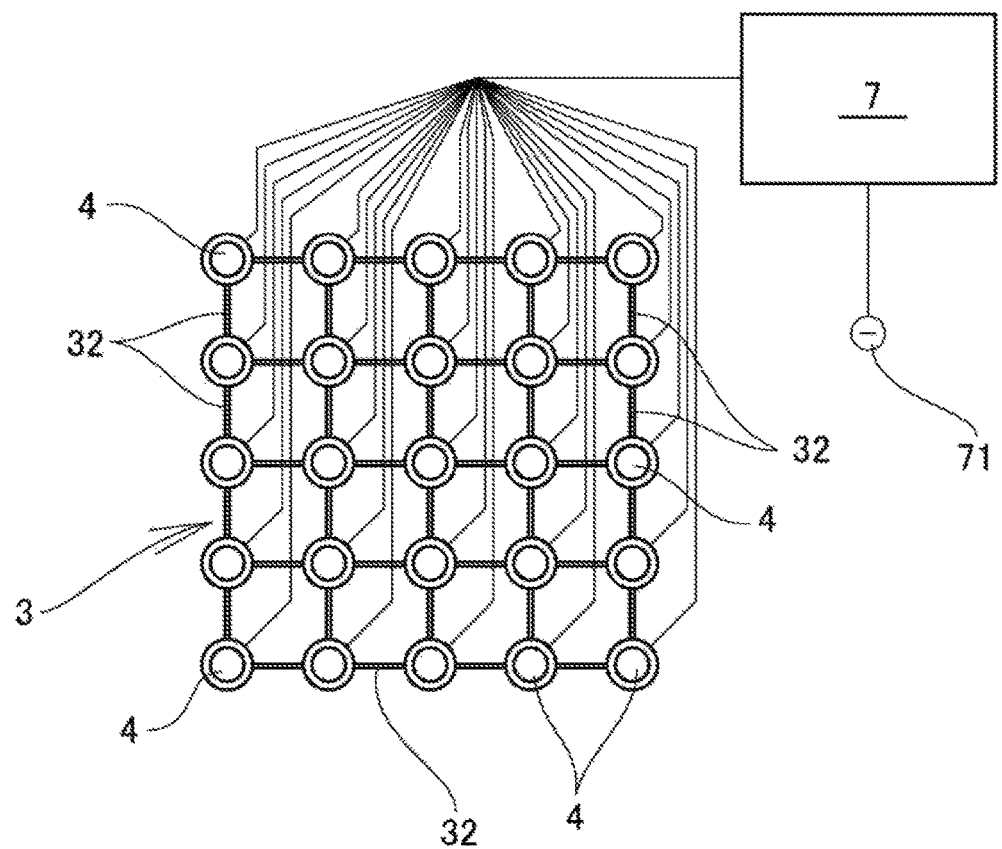
FIG. 4 is a planar view illustrating another example of an electrode sheet.
Figure 5:
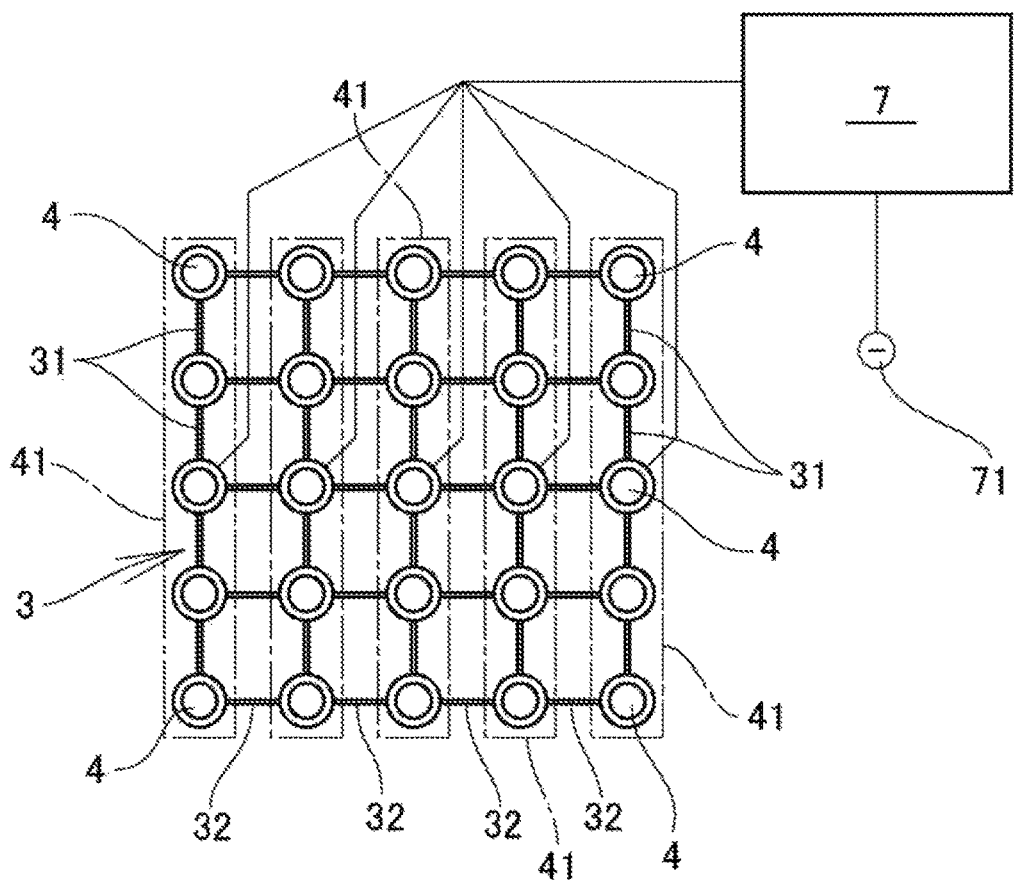
FIG. 5 is a planar view illustrating a further another example of an electrode sheet.
Figure 6:
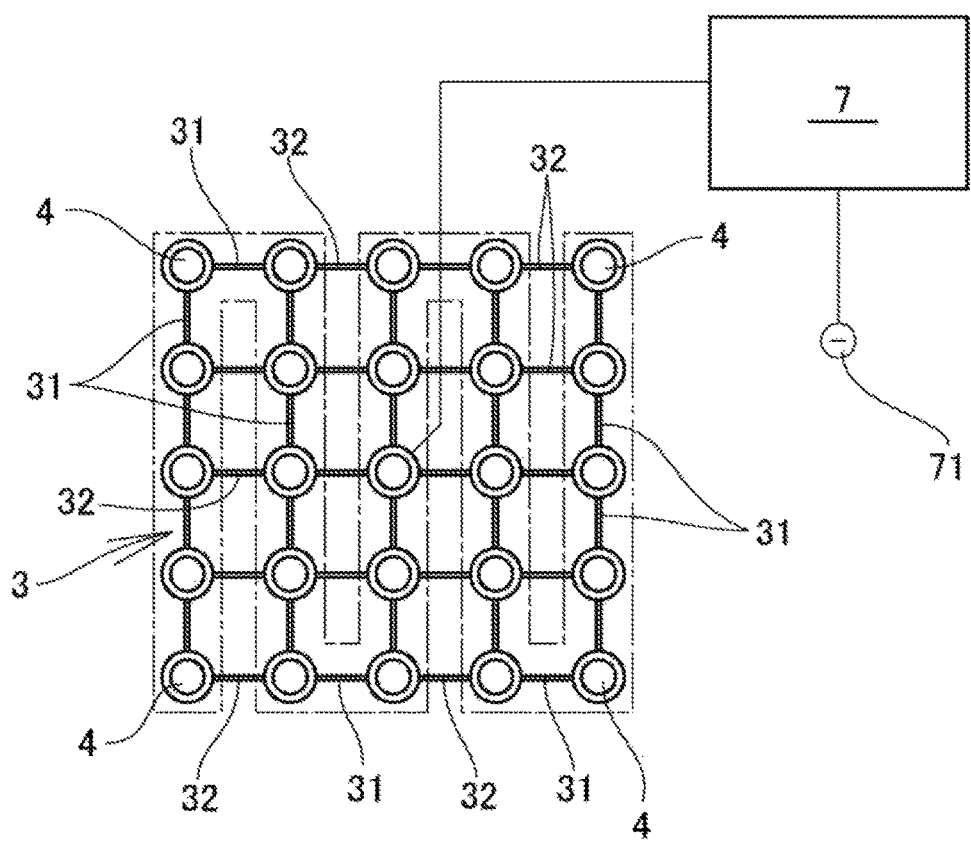
FIG. 6 is a planar view illustrating a further another example of an electrode sheet.

The stretching wires include the conductive stretching wires 31 which have conductivity and insulating stretching wires 32 which have insulating properties. An embodiment of the electrode sheet 3 is appropriately selected according to the application of the biological electrode 1, from an embodiment in which all of the stretching wires are the conductive stretching wires 31 as illustrated in FIGS. 3A and 3B, an embodiment in which all of the stretching wires are the insulating stretching wires 32 as illustrated in FIG. 4, and an embodiment in which a portion of the stretching wires are the conductive stretching wires 31 and the remainder of the stretching wires are the insulating stretching wires 32 as illustrated in FIG. 5 and FIG. 6.

The conductive stretching wire 31 is obtained by, for example, knitting a spirally-twisted conductive wire and an inversely-twisted, stretchable and flexible elastic fiber together. Accordingly, the conductive stretching wire 31 can be varied in shape in the line axis direction and the bending direction, and has restoring properties. The stretching wire 31 does not have a core material, and can be suitably deformed in the line axis direction and the bending direction.

It is noted that the conductive stretching wire 31 is not limited to the above-described embodiment, and may be obtained by, for example, mixing and kneading a conductive material with a material such as elastic resin, and processing the kneaded materials into the shape of a wire.

On the other hand, the insulating stretching wire 32 is constituted by elastic, insulating resin fibers, and can be deformed in the line axis direction and the bending direction while having restoring properties.

In the electrode sheet 3 illustrated in FIGS. 3A and 3B, the neighboring electrode bodies 4 are connected to each other via the conductive stretching wires 31, so that the electrode bodies 4 are electrically connected to each other, and the conductive stretching wires 31 between the electrode bodies 4 can be deformed in the line axis direction and the bending direction.

In this electrode sheet 3, the electrode body 4 located in the center is preferably provided with a connection terminal (not shown) and connected to the equipment 7. Accordingly, the electric resistance values from the center electrode body 4 to the electrode bodies 4 located in the same distance from the center electrode body 4 become uniform, thereby enabling the potential differences among the electrode bodies 4 to be reduced.

On the other hand, in the electrode sheet 3 illustrated in FIG. 4, all of the electrode bodies 4 are linked via the insulating stretching wires 32, and each of the electrode bodies 4 is connected to the equipment 7. Accordingly, the electrode bodies 4 are connected in parallel to the equipment 7, and electric power is uniformly supplied (a signal is uniformly applied) to the electrode bodies 4.

In the electrode sheet 3 illustrated in FIG. 5, the electrode bodies 4 which neighbor each other in one (the vertical direction in the mesh) of the intersecting directions are connected via the conductive stretching wires 31, and the electrode bodies 4 which neighbor each other in the other (the transverse direction in the mesh) of the intersecting directions are linked via the insulating stretching wires 32. The electrode sheet 3 includes a plurality of series circuit units 41 each constituted by the electrode bodies 4 which are sequentially disposed in the vertical direction. Each of the series circuit units 41 is to be connected in parallel to the equipment 7.

Also, in the electrode sheet 3 illustrated in FIG. 6, the electrode bodies 4 which neighbor each other in one (the vertical direction in the mesh) of the intersecting directions are connected via the conductive stretching wires 31, and the prescribed electrode bodies 4 which are located at the ends of the columns are connected to each other via the conductive stretching wires 31. Other neighboring electrode bodies 4 are linked via the insulating stretching wires 32. Accordingly, in the electrode sheet 3, all of the electrode bodies 4 are connected in series in a turn-around arrangement as indicated by dot-and-dash lines in FIG. 6.

It is noted that an embodiment of the electrode sheet 3 is not limited to the embodiments of FIG. 3A to 6, and any circuit suitable for an application may be formed by, for example, the arrangement of the conductive stretching wires 31 or the insulating stretching wires 32 and the combination thereof, and the number of electrode bodies 4 to be connected to the equipment 7 and the positions of the electrode bodies 4.

The conductive cloth portion 5 has the shape of a stretchable and flexible cloth or sheet formed with ultrathin chemical fibers such as nanofibers. Furthermore, conductive macromolecules are allowed to enter between the chemical fibers, so that the entire cloth portion has conductivity.

Also, the conductive cloth portion 5 includes a fixing unit that fixes the margin of the conductive cloth portion 5 to the insulating cloth portion 22. Since the conductive cloth portion 5 is fixed to the insulating cloth portion 22, the electrode sheet 3 is sandwiched between the insulating cloth portion 22 and the conductive cloth portion 5. Thus, the insulating cloth portion 22, the electrode sheet 3 and the conductive cloth portion 5 are integrated in a layered arrangement.

The unit for fixing the conductive cloth portion 5 to the insulating cloth portion 22 is not particularly limited. For example, fibers which constitute the conductive cloth portion 5 and fibers which constitute the insulating cloth portion 22 may be knitted, or the margin of the conductive cloth portion 5 may be heat-sealed, sewn, or pasted.

This conductive cloth portion 5 is superimposed on the electrode sheet 3, such that it remains in a state of being in contact with the electrode bodies 4. Thus, the conductive cloth portion 5 and the electrode sheet 3 can follow each other to be deformed while being electrically connected.

According to the biological electrode-equipped wearing tool 2 configured as described above, the insulating cloth portion 22 has stretchability. Therefore, the clothes 21 are brought into intimate contact with the surface of the living body 6 when worn. Accordingly, the biological electrode 1 integrated with the insulating cloth portion 22 is also brought into intimate contact with the living body 6.

At that time, the conductive cloth portion 5 made of fibers in the biological electrode 1 is in intimate contact with the surface of a living body. Thus, a favorable feel and a certain contact surface area with the living body 6 can be obtained.

Furthermore, the conductive cloth portion 5 in this biological electrode 1 has stretchability and flexibility, and thus follows the movement of the living body 6 to be deformed, so that the state of being in intimate contact with the living body 6 is maintained. Also, the stretching wires which link the neighboring electrode bodies 4 of the electrode sheet 3, that is, the conductive stretching wires 31 or the insulating stretching wires 32, have stretchability and flexibility. Accordingly, the electrode sheet 3 follows the deformation of the conductive cloth portion 5.

At that time, the electrode bodies 4 in a multipolar arrangement are always in contact with the conductive cloth portion 5. Therefore, an electrical distribution suitable for the circuit of the electrode sheet 3 can be obtained in any position of the conductive cloth portion 5.

It is noted that although an example in which the electrode body 4 located in the center of the electrode sheet 3 is to be connected to the equipment 7 has been mainly described in the above-described example, any of the electrode bodies 4 which constitute the electrode sheet 3 may be connected to the equipment 7 depending on the application.

Also, although an example in which clothes such as a shirt is used as the wearing tool 2 has been described in the above-described example, an embodiment of the clothes is not limited to the above-described example, and may have a shape of a vest, a belly band, or the like.

Furthermore, an embodiment of the wearing tool 2 is not limited to clothes, and may be an attachment tool (a so-called supporter) having a shape of a band, a tube, socks, or gloves for covering muscles, joints or ligaments.

Also, although the biological electrode-equipped wearing tool 2 has been described in the above-described example, the biological electrode 1 according to an embodiment of the present invention can also be applied to another object which is used in the state of being in contact with a living body, such as a chair and a bed, in addition to the wearing tool indicated in the above-described examples.

Also, a living body is not limited to the human body, and may be animals such as pets and livestock.

The invention claimed is:

1. A biological electrode adapted to be contacted with a surface of a living body and electrically connected to the living body, comprising:
    an electrode sheet having a plurality of electrode bodies including a hemispherical portion spaced apart from each other; and
    a stretchable conductive cloth portion superimposed on the electrode sheet, wherein
    the electrode sheet includes stretching wires that link neighboring electrode bodies, and has a shape of a stretchable and flexible mesh sheet, and
    the hemispherical portion of each of the plurality of electrode bodies are adapted to contact with the surface of the living body via the stretchable conductive cloth portion.

2. The biological electrode according to claim 1, wherein a portion or all of the stretching wires are conductive stretching wires.

3. The biological electrode according to claim 1, wherein an electrode body from among the plurality of electrode bodies that is located in a center of the electrode sheet is configured for connection to equipment.

4. The biological electrode according to claim 1, wherein all of the stretching wires are insulating stretching wires, and each of the plurality of electrode bodies is configured for connection to equipment.

5. A biological electrode-equipped wearing tool comprising a biological electrode integrated with an insulating cloth portion which constitutes a wearing tool, the biological electrode being adapted to be brought into intimate contact with a surface of a living body by wearing the wearing tool, wherein
    the biological electrode includes an electrode sheet having a plurality of electrode bodies including a hemispherical portion spaced apart from each other, and a stretchable conductive cloth portion superimposed on the electrode sheet,
    the electrode sheet includes stretching wires that link neighboring ones of the plurality of electrode bodies, and has a shape of a stretchable and flexible mesh sheet,
    the insulating cloth portion, the electrode sheet, and the stretchable conductive cloth portion are integrated in a layered arrangement, and
    the hemispherical portion of each of the plurality of electrode bodies are adapted to contact with the surface of the living body via the stretchable conductive cloth portion.

6. The biological electrode-equipped wearing tool according to claim 5, wherein a portion or all of the stretching wires are conductive stretching wires.

7. The biological electrode-equipped wearing tool according to claim 5, wherein an electrode body from among the plurality of electrode bodies that is located in a center of the electrode sheet is configured for connection to equipment.

8. The biological electrode-equipped wearing tool according to claim 5, wherein all of the stretching wires are insulating stretching wires, and each of the plurality of electrode bodies is configured for connection to equipment.

9. The biological electrode-equipped wearing tool according to claim 5, wherein the wearing tool is clothes.

10. The biological electrode-equipped wearing tool according to claim 5, wherein the wearing tool is an attachment tool having a shape of a band, a tube, socks, or gloves for covering muscles, joints or ligaments.

11. The biological electrode-equipped wearing tool according to claim 5, wherein the stretchable conductive cloth portion includes a fixing unit to fix a margin of the conductive cloth portion to the insulating cloth portion.

12. The biological electrode-equipped wearing tool according to claim 11, wherein the margin is at least one of heat-sealed, sewn and pasted.

13. The biological electrode-equipped wearing tool according to claim 5, wherein the stretchable conductive cloth portion is superimposed to remain in a state of being in contact with the plurality of electrode bodies such that the stretchable conductive cloth portion and the electrode sheet follow each other to be deformed while being electrically connected.

* * * * *